United States Patent [19]

Biollaz

[11] 4,309,423

[45] Jan. 5, 1982

[54] COMPOUNDS OF THE PREGNANE SERIES WITH AN OXYGEN FUNCTION IN THE 19-POSITION, PROCESSES FOR THEIR MANUFACTURE AND PHARMACEUTICAL PREPARATIONS CONTAINING THESE COMPOUNDS

[75] Inventor: Michel Biollaz, Riehen, Switzerland

[73] Assignee: Ciba-Geigy Corporation, Ardsley, N.Y.

[21] Appl. No.: 119,702

[22] Filed: Feb. 8, 1980

Related U.S. Application Data

[63] Continuation of Ser. No. 909,870, May 26, 1978, abandoned.

[30] Foreign Application Priority Data

May 31, 1977 [LU] Luxembourg ................. 77457

[51] Int. Cl.$^3$ ............................ A61K 31/56
[52] U.S. Cl. ............................. 424/242; 260/397.47; 260/239.5; 260/397.3; 260/397.4; 260/239.55 R
[58] Field of Search ................ /Steroids MS File; 424/242; 260/239.55, 239.57, 397.47

[56] References Cited

U.S. PATENT DOCUMENTS

| | | | |
|---|---|---|---|
| 3,039,926 | 6/1962 | Shull | 167/65 |
| 3,250,792 | 5/1966 | Wettstein et al. | 260/397.1 |
| 3,493,564 | 2/1976 | Kruger et al. | 260/239.55 |
| 3,849,404 | 11/1974 | Zadodski et al. | 260/239.57 |
| 4,213,902 | 7/1980 | Okushima et al. | 260/239.57 |

FOREIGN PATENT DOCUMENTS

| | | | |
|---|---|---|---|
| 1146651 | 4/1963 | Fed. Rep. of Germany | 260/239.57 |
| 2014244 | 9/1970 | Fed. Rep. of Germany | 260/397.1 |
| 2455272 | 5/1975 | Fed. Rep. of Germany | 260/397.1 |
| 1041534 | 7/1966 | United Kingdom | 260/239.57 |

OTHER PUBLICATIONS

Fieser et al., "Steroids", p. 708.
J. Org. Chem. 19, (1954), p. 1760, 29, (1964), p. 13046 and 35 (1970), p. 858.
Tetrahedron. 31 (1975), pp. 2151, 2157.
Djerassi et al., "Steroid Reactions", (1963), Holden-Day Inc., San Francisco, pp. 20, 21, 229–232.

Primary Examiner—Elbert L. Roberts
Attorney, Agent, or Firm—Michael W. Glynn; Theodore O. Groeger; Norbert Gruenfeld

[57] ABSTRACT

19-Oxygenated steroid compounds of the pregnane series of the formula I

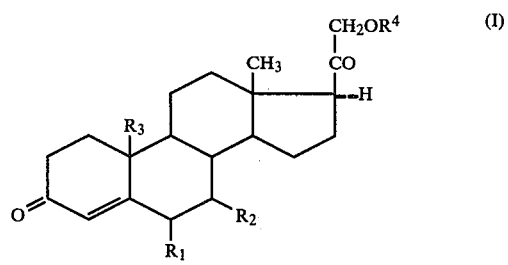

in which
 $R^1$ represents a hydrogen atom, and
 $R^2$ represents an α-oriented lower alkanoylthio group, or
 $R^1$ and $R^2$ together represent a carbon-carbon bond or an α- or β-oriented methylene radical,
 $R^3$ represents a free hydroxymethyl group or a hydroxymethyl group etherified by a lower alkyl or esterified by a lower alkanoyl; or represents a formyl group, a carboxyl group or a lower alkoxycarbonyl group, and
 $R^4$ represents a hydrogen atom or the acyl radical Ac of a carboxylic acid, and corresponding 1,2-dehydro derivatives have valuable aldosterone-antagonizing properties with a minimum effect on sexual functions. As the compounds reduce the excessive sodium retention and potassium excretion induced by aldosterone, they are especially useful as the active ingredient in pharmaceutical preparations for alleviating diseases involving hyperaldosteronism in man and other warm-blooded animals.

19 Claims, No Drawings

COMPOUNDS OF THE PREGNANE SERIES WITH AN OXYGEN FUNCTION IN THE 19-POSITION, PROCESSES FOR THEIR MANUFACTURE AND PHARMACEUTICAL PREPARATIONS CONTAINING THESE COMPOUNDS

This is a continuation of application Ser. No. 909,870 filed May 26, 1978 now abandoned.

The invention relates in particular to pharmaceutical preparations containing at least one steriod compound of the pregnane series of the formula

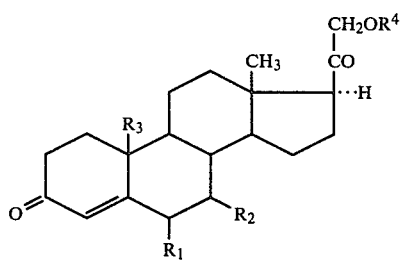

in which $R^1$ represents a hydrogen atom, and $R^2$ represents an α-oriented lower alkanoylthio group, or $R^1$ and $R^2$ together represent a carbon-carbon bond or an α- or β-oriented methylene radical, $R^3$ represents a free hydroxymethyl group or a hydroxymethyl group etherified by a lower alkyl or esterified by a lower alkanoyl; or represents a formyl group, a carbonyl group or a lower alkoxycarbonyl group, and $R^4$ represents a hydrogen atom or the acyl radical Ac of a carboxylic acid, and/or a corresponding salt and/or a 1,2-dehydro derivative thereof. The invention furthermore relates to processes for the manufacture of these preparations, and to the therapeutic use of these compounds and to preparations for warmblooded animals, especially man.

The pharmaceutical preparations according to the invention are distinguished by advantageous biological properties. In particular, they have a pronounced aldosterone-antagonistic action through reducing the excessive sodium retention and potassium excretion caused by aldosterone. As potassium-conserving diuretic agents their use is therefore important in the therapy of illnesses that involve a disturbed mineral/-water balance, for example, in the treatment of cardiac insufficiency, disrhythmia resulting from potassium deficiency, for *Cor pulmonale*, cirrhosis of the liver, ascites prophylaxis, diabetes mellitus and hypertension.

Steroids having an aldosterone-antagonising effect known so far are spiroxane derivatives, cf., for example, Fieser and Fieser: Steroids, page 708 (Reinhold Publ. Corp., New York, 1959) and British Pat. No. 1 041 534; also known are corresponding 17β-hydroxy-21-carboxylic acids and their salts, which have an analogous action, cf., for example, U.S. Pat. No. 3,849,404. Compounds of this type hitherto used in therapy have a considerable disadvantage, however, for they always have a certain sexual-specific activity which, during the customary long -term therapy sooner or later has an adverse effect. Particularly undesirable disturbances are those attributable to the antiandrogenic activity of the known antialdosterone preparations.

It is also generally known that 21-hydroxyregn-4-ene-3,20-dione (desoxycorticosterone) and its 21-esters which all have a basic structure (4,5-unsaturated 3-ketone, hydroxyacetyl side chain) analogous to that of the compounds of the invention, reveal a physiological effect similar to that of aldosterone, namely especially sodium retention and potassium excretion. Also aldosterone itself has these characteristic structural features. Physiological activity of the same kind was also discovered in 19-hydroxydesoxycorticosterone (19,20-dihydroxypregn-4-ene-3,20-dione), but amounted only to about 4% of the activity of the 19-unsubstituted parent substance (desoxycorticosterone), cf. J. Org. Chem. 31, 2427 (1954). No biological activity has been described for other known 19-oxygenated analogues of desoxycorticosterone, such as those with a 10β-acetoxymethyl, 10β-formyl or 10β-carboxyl group; these compounds were used solely as intermediates.

A few compounds of the type characterised by the formula I have also individually been proposed as intermediates or starting materials not having any biological activity. For example, in the description of U.S. Pat. No. 3,250,792, compounds of the formula I, in which $R^1$ and $R^2$ together form a C—C bond, $R^3$ represents a hydroxymethyl or formyl group, and $R^4$ represents an acyl group, were considered as possible intermediates for corresponding 19-norsteroids. Compounds of the formula I, in which $R^1$ and $R^2$ together form a C—C bond, $R^3$ represents the formyl group, and $R^4$ represents hydrogen or acyl, have been proposed in German Offenlegungsschrift No. 2 014 244 as starting materials for direct conversion into corresponding 19-norsteroids. In U.S. Pat. No. 3,849,402, a general formula of a steroid-4,6-diene is indicated and among the numerous meanings of the substituents in the 10β-and 17β-position thereof there are those that would correspond to individual features of the compounds of the above-characterised formula I, for example, in which $R^1$ and $R^2$ together form a C—C bond, or $R^3$ represents a hydroxymethyl group, which may also be etherified by lower alkyl or esterified by an acetyl, trialkylacetyl, monohaloacetyl or trihaloacetyl radical, or $R^4$ represents one of these acetyl radicals. However, these structural elements were not so combined that they would relate in a narrower or more specific selection to any one of the compounds of the formula I. A similar use for analogously characterised starting materials is also described in German Offenlegungsschrift No. 2 455 272; but among the starting materials for the synthesis of the cardenolidelactone ring, 19-acetoxy-21-hydroxypregna-4,6-diene-3,20-dione has been specifically proposed in this publication, and there is no reference whatsoever either to origin or method of manufacture or physical data of the compound. None of these four patent specifications makes any mention of biological activity or gives any indication of pharmaceutical use.

By means of biological tests in the dosage range of approximately 5–50 mg/kg it has now been found that the 19-oxygenated compounds of the above-characterised formula I surprisingly have a pronounced aldosterone-antagonistic action, whereas the undesired side effect on the balance of semal hormones, observed in antialdosterone preparations of the prior art is practically non-existent. For example, 19,21-dihydroxypregna-4,6-diene-3,20-dione 19-acetate and 19,21-diacetate, as well as 7α-acetylthio-19,21-dihydroxy-pregn-4-ene-3,20-dione 19-acetate exhibit a marked aldosterone-antagonistic action when administered perorally in a dose of about 5 mg/kg (Kagawa test with adrenalectomised male rats), whereas there is still no detectable anti-androgenic action on peroral administration of doses above 50 mg/kg (castrated male rats treated with testosterone propionate). When 19,21-dihydroxypregna-4,6-diene-3,20-dione is administered, the mean antialdosteroneactive dosage is approximately 5 mg/kg, and no sexual-specific side effects, for example those according to the specified test on castrated rats, could be detected even after peroral administration of three doses of 60 mg/kg each.

Pharmaceutical preparations of the invention to be singled out for special mention are those that contain at least one compound of the formula I in which $R^1$ and $R^2$ have the meanings given above, $R^3$ represents a free hydroxymethyl group or a hydroxymethyl group esterified by lower alkanoyl, and $R^4$ represents hydrogen or acyl, preferably those that are 1,2-saturated.

Particularly preferred preparations are those that contain at least one 1,2-saturated compound of the formula I in which $R^1$ and $R^2$ together represent a carbon-carbon bond, $R^3$ represents a hydroxymethyl or lower alkanoyloxymethyl group and $R^4$ represents hydrogen or lower alkanoyl, especially those in which $R^3$ is a hydroxymethyl group and $R^4$ is hydrogen, or $R^3$ is a lower alkanoyloxymethyl group and $R^4$ is lower alkanoyl, whilst lower alkanoyl radicals derived from linear lower alkanoic acids are particularly preferred. Specific mention may be made of preparations containing 19,21-dihydroxypregna-4,6-diene-3,20-dione, the 19-acetate, 21-acetate or 19,21-diacetate thereof.

Particularly preferred preparations are also those containing at least one 1,2-saturated compound of the formula I in which $R^1$ represents hydrogen, $R^2$ α-acetylthio, $R^3$ hydroxymethyl, lower alkanoyloxymethyl, especially acetoxymethyl, or lower alkoxycarbonyl, especially methoxycarbonyl, and $R^4$ represents hydrogen or lower alkanoyl, especially acetyl, particularly those that contain 7α-acetylthio-19,21-dihydroxypregn-4-ene-3,20-dione, its 19-acetate, 21-acetate or 19,21-diacetate.

Particularly preferred preparations are in addition those containing at least one 1,2-saturated compound of the formula I, in which $R^1$ and $R^2$ together represent a methylene group in the β-position, $R^3$ represents hydroxymethyl, lower alkanoyloxymethyl, especially acetoxymethyl or lower alkoxycarbonyl, especially methoxycarbonyl, and $R^4$ represents hydrogen or lower alkanoyl, especially acetyl; especially those containing 19,21-dihydroxy-6β,7β-methylenepregn-4-ene, 3,20-dione, the 19-acetate, 21-acetate or 19,21-acetate thereof.

In general, those preparations are preferred that contain at least one of the compounds of the formula Ia referred to hereinafter as preferred.

The invention also relates to processes for the manufacture of 19-oxygenated steroids of the pregnane series of the initially-characterised formula I, especially of compounds of the formula Ia

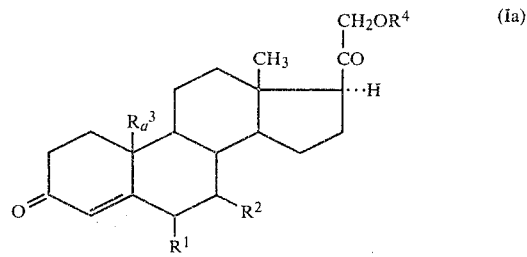

in which
$R^1$ represents a hydrogen atom, and
$R^2$ represents an α-oriented lower alkanoylthio group, or
$R^1$ and $R^2$ together represent a carbon-carbon bond or an α- or β-oriented methylene radical,
$R_a^3$ represents a free hydroxymethyl group or a hydroxymethyl group etherified by a lower alkyl or esterified by a lower alkanoyl; or represents a carboxyl group or a lower alkoxycarbonyl group, and
$R_a^4$ represents a hydrogen atom or the acyl radical Ac of a carboxylic acid,
and of corresponding salts and 1,2-dehydro derivatives, and these compounds themselves including the salts and 1,2-dehydro derivatives. Compounds to be highlighted are those of the formula Ia, including the corresponding 1,2-dehydro derivatives, in which $R^1$, $R^2$, $R_a^3$ and $R^4$ have the meanings given above, with the proviso that in 1,2-saturated compounds in which $R^1$ and $R^2$ represent a C—C bond and $R^4$ represents an acyl radical Ac, $R_a^3$ represents a hydroxymethyl group etherified by a lower alkyl or esterified by a lower alkanoyl, a carboxyl group or a lower alkoxycarbonyl group, and in 1,2-saturated compounds in which $R^1$ and $R^2$ represents a C—C bond and $R^4$ represents a hydrogen atom, $R_a^3$ represents a free hydroxymethyl group or, preferably, a hydroxymethyl group etherified by a lower alkyl or esterified by a lower alkanoyl other than acetyl, or represents a carboxyl group or a lower alkoxycarbonyl.

Of these compounds the following are preferred: 1,2-saturated compounds of the formula Ia, in which $R^1$ and $R^2$ have the meanings given above, $R_a^3$ is a free hydroxymethyl group or a hydroxymethyl group esterified by lower alkanoyl, and $R^4$ is hydrogen or acyl Ac, especially with the proviso that in compounds in which $R^1$ and $R^2$ together represent a C—C bond and $R^4$ represents an acyl radical Ac, $R_a^3$ is a lower alkanoyloxymethyl radical, and in compounds in which $R^1$ and $R^2$ together represent a C—C bond and $R^4$ represents a hydrogen atom, $R_a^3$ represents a free hydroxymethyl group or a hydroxymethyl group esterified by lower alkanoyl other than acetyl.

Particularly preferred compounds are compounds of the formula Ia, in which $R^1$ represents hydrogen and $R^2$ represents α-acetylthio or $R^1$ and $R^2$ together represent a β-oriented methylene group, $R_a^3$ represents hydroxymethyl, lower alkanoyloxymethyl or lower alkoxycarbonyl, especially methoxycarbonyl, and $R^4$ represents hydrogen or lower alkanoyl, whilst possible lower alkanoyl radicals in the symbols $R_a^3$ and $R^4$ are in particular linear lower alkanoyl radicals, especially acetyl.

Especially preferred compounds are also compounds of the formula IA

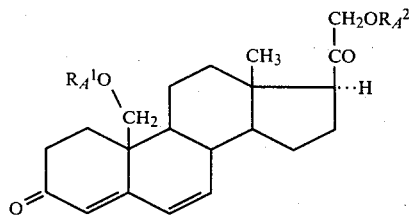

in which $R_A{}^1$ represents a lower alkanoyl radical and $R_A{}^2$ is an acyl radical Ac, or $R_A{}^1$ is a lower alkanoyl radical other than acetyl and $R_A{}^2$ is a hydrogen atom, or each of $R_A{}^1$ and $R_A{}^2$ represents a hydrogen atom, whilst a lower alkanoyl radical is preferred as acyl radical Ac, and particularly preferred lower alkanoyl radicals are linear lower alkanoyl radicals, especially the acetyl radical. To be singled out for specific mention are 19,21-dihydroxypregna-4,6-diene-3,20-dione and 19,21-dihydroxypregna-4,6-diene-3,20-dione 19,21-diacetate, and all the compounds of the formulae I and Ia mentioned in the Examples.

Unless otherwise indicated, the expression "lower", used in connection with the definition of a compound or of a substituent, refers to a compound or a substituent containing not more than 4 carbon atoms.

In the above-characterised formula I, the acyl radical Ac is derived from the carboxylic acids customary in steroid chemistry, for example aliphatic monocarboxylic acids having 1–8 carbon atoms, such as valeric, isovaleric, trimethylacetic, hexanoic, 2,2-dimethylbutyric and heptanoic acid, and especially from straight or branched lower alkanoic acids, such as formic, propionic, butyric, isobutyric and, especially, acetic acid. Included, however, all also acids that are unsaturated and/or are substituted in the usual manner, for example: phenyl- and cyclohexylacetic acid, phenoxyacetic acid, β-cyclopentylpropionic acid, haloacetic acids such as chloroacetic acid and trifluoroacetic acid, aminoacetic acid, α- or β-hydroxypropionic acid, benzoic acid and aliphatic dicarboxylic acids, such as succinic and glutaric acid, or phthalic acid, of which the second carboxylic group may occur in the form of a salt, for example with an alkali metal such as potassium or sodium.

A lower alkanoylthio group is derived from the specified lower alkanoic acids and is especially the acetylthio group.

A lower alkyl radical is preferably one having a straight carbon chain, for example ethyl, propyl, butyl and especially methyl. Preferred lower alkoxy radicals correspond to the preferred lower alkyl radicals mentioned; the methoxy radical is particularly preferred.

Those compounds of the invention that contain a free carboxyl group may, as already mentioned, also occur in the form of their salts. Possible salts are especially metal and ammonium salts, such as alkali metal and alkaline earth metal salts, for example sodium, calcium, magnesium and, preferably, potassium salts, or ammonium salts derived from ammonia or a suitable, preferably physiologically tolerable, organic nitrogen-containing base. Suitable bases are amines, such as lower alkylamines, for example triethylamine; hydroxy-lower alkylamines, for example 2-hydroxyethylamine, di-(2-hydroxyethyl)-amine or tri-(2-hydroxyethyl)-amine; cycloalkylamines, for example dicyclohexylamine; or benzylamines, for example benzylamine and N,N′-dibenzylethylenediamine, and nitrogen-containing heterocyclic compounds, for example those of aromatic character such as pyridine or quinoline, or those having an at least partially saturated heterocyclic ring, such as N-ethylpiperidine, morpholine, piperazine or N,N′-dimethylpiperazine.

The processes for the manufacture of compounds of the initially characterised formulae I and Ia and of corresponding salts and 1,2-dehydro derivatives are known per se as conventional methods is steroid chemistry.

Compounds of the formula I are obtained by isomerising a corresponding compound of the 17α-pregnane series of the formula II

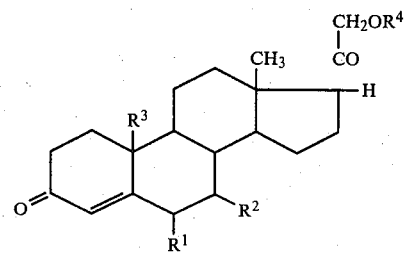

in which $R^1$, $R^2$, $R^3$ and $R^4$ have the meanings given above, by treating it with an enolising agent. An enolising agent is, for example, a strong base, such as a quaternary organic hydroxide, for example tetraethylammonium hydroxide or N,N-dimethylpiperidinium hydroxide, or a hydroxide or alcoholate, such as a phenoxide or lower alkoxide, of an alkali metal or alkaline earth metal, especially of sodium or potassium, such as, in particular, potassium and sodium hydroxide, sodium methoxide and ethoxide, and potassium tert.-butoxide, and also potassium and sodium carbonate. An enolising agent is especially also a strong acid, for example a protic acid, such as a hydrohalic acid, in particular hydrochloric acid and hydrobromic acid, also, sulphuric acid, perchloric acid, or an organic sulphonic acid, for example benzenesulphonic acid, p-toluenesulphonic acid or p-bromosulphonic acid, and also a Lewis acid, such as boron trifluoride, or boron trifluoride etherate, pyridinium chloride etc. and a carboxylic acid of medium strength, such as oxalic acid, formic acid or thioacetic acid. The isomerisation is carried out in a manner known per se, usually in an organic solvent under anhydrous conditions. Ester bonds which may be present in the molecule, such as acyloxy and alkoxycarbonyl groups, can be cleaved in the course of this process; in order to avoid this, it is preferable to use a catalytic amount of the enolising agent and to carry out the process in an aprotic, especially anhydrous, medium.

The starting materials of the formula II can be obtained by methods that are known per se, for example by synthesising the 17α-(2-hydroxyacetyl) side chain starting from corresponding 17-oxo compounds of the formula III given below and proceeding through, for example, 17α-cyano and 17α-formyl or 17α-carboxyl compounds in the manner described hereinafter for 17β-isomers.

Compounds of the formula I are also obtained by introducing the optionally acylated 2-hydroxyacetyl side chain into a corresponding 17-oxo compound of the formula III

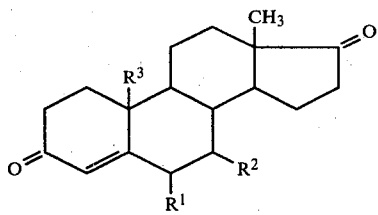

in which $R^1$, $R^2$ and $R^3$ have the meaning given above. The introduction of the hydroxyacetyl side chain is carried out in a manner known per se, for example by a stepwise synthesis via the corresponding 17β-cyano compounds. These are obtainable from the 17-oxo compound, for example by the addition reaction of hydrogen cyanide to the 17-oxo group, dehydration of the resulting mixture of epimeric 17-cyanohydrins to form a 16,17-unsaturated 17-cyano compound and saturation of the double bond by catalytic hydrogenation. Alternatively, the 17-cyano compound can be formed directly in accordance with the method published in Tetrahedron 31, 2151 and 2157 (1975) by the addition reaction of tosylmethyl isocyanide (Ts—$CH_2$—N=C) with the 17-oxo compound in the presence of a strong base. According to one variant, this 17-cyano compound can be hydrolysed to form the corresponding 17-carboxylic acid which then, in the form of the corresponding acid chloride, yields with diazomethane the corresponding diazoketone (a 21-diazo-20-oxo compound), which by treatment with a carboxylic acid of the formula AcOH, in which Ac has the meanings given above, especially with acetic acid, yields the desired final product of the formula I. In another variant, the 17-cyano compound can firstly be reduced to form a corresponding 17-formyl compound (17-carboxaldehyde), for example with diisobutyl aluminium hydride of the formula $[(CH_3)_2CHCH_2]_2AlH$ according to a method described in J. Org. Chem. 35, 858 (1970) and J. Org. Chem. 29, 3046 (1964). (This 17-formyl compound is alternatively also obtainable from the 17-oxo compound by the reaction according to Wittig with methoxymethylenetriphenylphosphorane and by acid-catalysed hydrolysis of the intermediate 17-methoxymethyl compound). The 17-formyl compound can then be reacted, for example with a reagent that is obtained from formaldehyde dimethylmercaptal S-oxide ($CH_3$—S—$CH_2$—SO—$CH_3$) by metallisation with an organo-alkali metal compound, such as in particular with butyl lithium. The 20-hydroxy-21-aldehyde protected at the aldehyde group, which is obtained as intermediate and has the partial formula

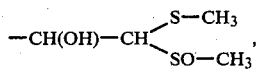

is then hydrolysed to form the desired compound of the formula I by acid catalysis and simultaneous isomerisation of the oxygen functions. The hydrolysis is carried out under the customary conditions for acid hydrolysis, for example with an aqueous inorganic acid, such as hydrochloric acid, in a water-miscible organic solvent, optionally at elevated temperature up to the boiling temperature of the reaction mixture. The customary desulphurisation agents, such as cadmium and mercury salts, are not needed for the hydrolysis.

Preferably, the oxygen-containing functional groups not participating in the synthesis, particularly oxo groups, such as, especially, the 3-oxo group, are temporarily protected in a conventional manner during the above-described reactions; thioketalisation, for example with ethylene dithiol, is particularly advantageous for the protection of the 3-oxo group.

The 17-oxo compounds of the formula III used as starting materials are generally known or, if they are not known, can be obtained, like the known compounds, by known processes.

Compounds in which $R^1$ and $R^2$ together represent a C—C, bond, and the 1,2-dehydro derivatives thereof, can also be obtained by a general method by dehydrogenating in the 6,7-position, and optionally at the same time also in the 1,2-position, a corresponding 6,7-saturated starting compound of the formula IV

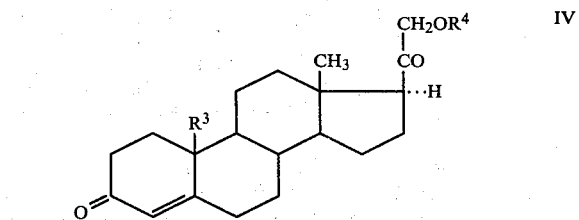

in which $R^3$ and $R^4$ are as defined above, or a 1,2-dehydro derivative, or a 5-enol ether of the 1,2-saturated compounds, the 3-ether group optionally present is split. The 6,7-dehydrogenation is carried out by methods known per se, for example by treatment with a quinone having a dehydrogenating action, for example chloranil or, especially, 2,3-dichloro-5,6-dihydro-1,4-benzoquinone. When using the former, the process is preferably carried out at boiling temperature in organic solvents, for example aromatic hydrocarbons, such as benzene or xylene; lower aliphatic alcohols, such as ethanol, propanol or tert.-butyl alcohol; lower aliphatic ketones, such as acetone or butan-2-one; aliphatic esters, such as ethyl acetate; or cyclic ethers, such as dioxan or tetrahydrofuran. When dichlorodicyanobenzoquinone is used, the process is preferably carried out in the presence of hydrochloric acid, at or below room temperature, in a water miscible organic solvent, for example one of those mentioned above.

It is also possible to react in an analogous manner a corresponding 3-enol ether, preferably a lower alkyl, such as methyl or ethyl, enol ether, or to dehydrogenate it to the desired final product by treatment with manganese dioxide, preferably in a halogenated hydrocarbon, such as chloroform or dichloromethane, whereby the ether-forming radical is split off simultaneously. The 3-ethers used can be obtained according to generally known methods, preferably by treating a corresponding 4,5-unsaturated 3-ketone with a corresponding formic acid orthoester, such as methyl orthoformate or ethyl orthoformate, with acid catalysts.

The 1,2- and 6,7-dehydrogenation of the 1,2-saturated 4-en-3-one compounds or their 3-enol ethers optionally carried out simultaneously is effected in a manner known per se by treatment with a quinone having a dehydrogenating action, especially 2,3-dichloro-5,6-dicyano-1,4-benzoquinone. Preferably, the latter reactant is allowed to act at the boil for several, for example 6-24 hours; the same organic solvents as mentioned for the choranil dehydrogenation can be used.

The starting compounds of the formula IV are known or they can be obtained by processes known per se in analogous manner.

6,7-unsaturated compounds of the formula I, in which $R^1$ and $R^2$ together represent a C—C bond, $R^3$ represents a lower alkanoyloxymethyl group and $R^4$ represents an acyl group Ac, can also be produced by reacting a corresponding 6β,19-epoxide of the formula V

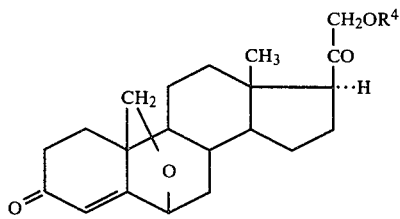

in which $R^4$ has the meaning given above, according to the method in German patent No. 1 196 651, with an acylating agent derived from a lower alkanoic acid in an anhydrous medium in the presence of a strongly acid catalyst. The acylating agent may be the acid itself, such as formic acid, or, preferably, a reactive derivative of the lower alkanoic acid, such as an anhydride and especially a symmetric anhydride, is used. A strongly acid catalyst is preferably an oxygen-containing acid, such as sulphuric acid, perchloric acid or an organic sulphonic acid, for example p-toluenesulphonic acid, p-bromobenzenesulphonic acid or benzenesulphonic acid; it is possible to use as solvent lower alkanoic acids, especially those that correspond to the acylating agent; the reaction may also advantageously be carried out in aprotic solvents, for example hydrocarbns, especially aromatic hydrocarbons, such as benzene or toluene, or in halogenated aliphatic hydrocarbons, such as especially chloroform and methylene chloride, for which temperatures of approximately 0° up to the boiling temperature of the reaction mixture, but preferably room temperature, are employed. If a starting material of the formula V in which $R^4$ is a hydrogen atom is used in the reaction, this is simultaneously exchanged for the acyl radical of the acylating agent.

The starting substances of the formula V are known or can be obtained according to known analogy processes.

The compounds of the formula I can also be obtained be removing the protective group(s) in a corresponding derivative having a protected, especially ketalised or thio-ketalised, 3-and/or 20-oxo group, with liberation of the oxo group or groups.

Suitable derivatives having a protected 3-oxo group are 3-ketals and especially 3-thioketals. The preferred 3-ketals are those derived from lower alkanols, such as methanol or ethanol, and especially from α- or β-glycols, such as propane-1,2-diol or propane-1,3-diol, butane-1,2-diol or butane-2,3-diol, and especially ethylene glycol. Suitable 3-thioketals are especially those derived from sulphur analogues of the glycols mentioned hereinbefore; 3,3-ethylenedithio derivatives are particularly preferred. Thioketals and especially ketals of the kind mentioned above are also suitable for the protection of the 20-oxo group.

Removal of these protective groups is carried out in a manner known per se by hydrolysis, preferably under the general conditions of acid catalysis. In the case of thioketals, however, the process is preferably carried out with the addition of a sulphur-binding compound, for example a metal salt, especially a heavy metal salt such as cadmium carbonate and/or mercury(II) chloride. Since the latter compound has a strongly acid reaction in the presence of water, when it is used no additional acid is necessary as catalyst.

If desired, the compounds obtained within the scope of the above-characterised final products can be converted into one another.

6,7-dehydro compounds of the formula I, in which $R^1$ and $R^2$ together represent a C—C bond, can, if desired, be converted by the addition reaction with a lower alkanethioic acid into the corresponding final products in which $R^1$ represents a hydrogen atom and $R^2$ represents an α-oriented lowr alkanoylthio group. The addition reaction is carried out in a manner known per se; preferably the 6,7-dehydro compound in question is heated in excess thiocarboxylic acid (lower alkanethioic acid), opitonally while irradiating with ultra-violet light. Usually the reaction proceeds at an acceptable speed at temperatures as low as a little above room temperature, for example, at about 50°; accordingly, when a lower-boiling thiocarboxylic acid is used, for example especially thioacetic acid, it is advantageous to carry out the reaction at the boiling temperature; when using higher-boiling thiocarboxylic acids, on the other hand, it is advantageous to maintain the reaction temperature at approximately 90°–100° C. The reaction times required in such a case may extend to a number of hours, but guarantee adequate reaction under mild conditions. In a typical process the resulting product crystallises directly on cooling, optionally after previous evaporation of excess reactant; if desired, however, the product may be purified or isolated in the usual manner, for example by chromatography. This addition reaction produces predominantly a single isomer, which on account of the analogy with other known similar compounds is allotted the structure specified above ($R^1$ is hydrogen, $R^2$ is an α-oriented lower alkanoylthio group) in accordance with the present state of knowledge. The factual data of the description which relate to products of this type, should, however, in the event of any subsequent allocation of another structure, remain valid.

6,7-dehydro compounds of the formula I in which $R^1$ and $R^2$ together represent a C—C bond, may, if desired, be converted by the addition of a methylene group into the corresponding final products, in which $R^1$ and $R^2$ together represent the 6α,7- or especially 6β,7-methylene group. The addition reaction is carried out by methods known per se; a preferred variant, however, is that in which a corresponding above-mentioned 6,7-dehydro compound is reacted with dimethyloxosulphonium methylide. This variant also has the important advantage that in the case of compounds having a free 19-hydroxyl group it has a very high stereo-specificity and affords predominantly 6,7-methylene compounds with the preferred β-configuration of the methylene group. The reaction is, for example, advantageously carried out by bringing together in an inert gas, such as nitrogen, and with the exclusion of moisture, a dispersion of sodium hydride in mineral oil and trimethylsulphoxonium iodide and subsequently adding dimethyl sulphoxide, whereupon the dimethyloxosulphonium methylide is formed. To this reagent, which is produced in situ, is added the 6,7-unsaturated starting steroid in the molar ratio (reagent:steroid) of about 1:1 to 5:1. The reaction is allowed to proceed at approximately room temperature and the reaction mixture is diluted with water. The steroid is the isolated by conventional methods. In the case of final products that contain alkali-sensitive groups, such as ester groups, the decomposition of the reaction mixture will be advantageously carried out in such a manner that the pH remains as far as possible in the neutral or weakly acid range.

It is also possible to dehydrogenate 1,2-saturated compounds to form the corresponding 1,2-dehydro derivatives in a manner known per se. For this purpose biological dehydrogenating processes may be used, for example dehydrogenation by means of the micro-organisms *Corynebacterium simplex* or *Septomyxa affinis* or their enzyme systems, or treatment with selenium dioxide in an organic solvent, for example tert.-butyl alcohol. The reaction is preferably carried out, however, with 2,3-dichloro-5,6-dicyano-1,4-benzoquinone, for example as described for the simultaneous 1,2- and 6,7-dehydrogenation.

Compounds having a free carboxyl group may be converted in a manner known per se into the corresponding salts by treatment with a base, for example ammonia, an alkali metal or alkaline earth metal base, or with an organic base, for example one of those mentioned above; if a free acid is desired, this is liberated by acidifying a salt. The alkali metal and alkaline earth metal bases used are, for example, corresponding hydroxides, such as sodium and especially potassium hydroxide, carbonates, such as sodium and potassium carbonate, or bicarbonates, such as sodium and potassium bicarbonate.

The oxygenated radical $R^3$ in the 10$\beta$-position and the $OR^4$ group in the 21-position in the compounds of the formula I can, if desired, be converted into another radical within the definition of the symbols $R^3$ and $R^4$ respectively; in particular, a hydroxyl group can be esterified or etherified or an esterified hydroxyl group can be liberated, the 10$\beta$-hydroxymethyl group can be oxidised to form the formyl group or to form the carboxyl group and the formyl group can be oxidised to form the carbonyl group, the carboxyl radical can be esterified and an esterified carboxyl radical can be set free. All these conversions are carried out in a manner known per se and can also be effected in suitable combinations, and optionally with conventional temporary protection of other functional groups present, such as, in particular, the 3- and/or 20-oxo group as well as the 21-hydroxyl group.

In the description of this specification conventional protection of the oxygen-containing functional groups is to be understood as meaning the conversion of a hydroxyl group or carboxyl group into an esterified form, and of an oxo group into an acetal or ketal, or into a thioacetal or thioketal, while both the introduction and the removal of the protective group are effected in a generally known manner.

Suitable advantageous steps for protecting the 20- and also the 3-oxo groups are in particular ketalisation and thioketalisation. The reactions are carried out in a manner known per se, especially under the conditions of acid catalysis and optionally using dehydrating agents or azeotropic distillation. Ketalisation is carried out for example with lower alkanols such as methanol or ethanol, and especially $\alpha$- and $\beta$-glycols, such as propane-1,2-diol or propane-1,3-diol and butane-1,2-diol or butane-2,3-diol, and especially ethylene glycol, or reactive derivatives of these alcohols, such as acetals or ketals, especially those in which the carbonyl component is readily volatile, for example 2,2-dimethyl-1,3-dioxolane. It is possible in an analogous manner, using sulphur analogues of the above-mentioned alcohols as starting materials, especially ethane-1,2-dithiol or a reactive derivative thereof, to obtain analogous thioketals.

The esterification or etherification of hydroxyl groups to be carried out, if desired, is likewise effected in a manner known per se. For esterification, the compound to be esterified is, for example, treated with excess acid itself, such as with formic acid, or with a reactive derivative thereof, for example with a derivative of one of the above-specified acids, especially with an anhydride or acid halide, such as acid chloride, advantageously in the presence of a tertiary base, such as pyridine, quinoline or N-ethylpiperidine. For etherification, the compounds to be etherified are, for example, treated with reactive derivatives of alcohols, for example with esters with strong acids, such as halides, sulphates or sulphonic acid esters, the alcohol component used being in particular a lower alkanol, such as especially methanol and ethanol.

The subsequent liberation of the protected oxygen-containing functional groups is carried out in a manner known per se by hydrolysis. Acetal and ketal groups are preferably hydrolysed under the general conditions of acid catalysis. Thioacetals and thioketals are also hydrolysed in this manner, preferably as specified above.

Esterified hydroxyl groups, whether in an acylated hydroxyl group or an esterified carboxyl group, may also be hydrolysed under acid conditions; preferably, however, they are hydrolysed by catalysis with a base. The basic catalysts preferably used are hydroxides, carbonates or bicarbonates of alkali metals or alkaline earth metals, especially sodium or potassium. Since the 21-positioned hydroxyl group can be liberated under milder conditions of base hydrolysis as catalyst than the 19-positioned hydroxyl group, it is possible to hydrolyse and esterified 21-hydroxyl group selectively whilst retaining a similarly esterified 19-hydroxyl group. On the other hand, it is also possible to achieve selective liberation of the 19-hydroxyl group, if the 21-hydroxyl group is esterified with an acyl radical that is difficult to hydrolyse, for example the benzoyl radical.

The esterification of the carboxyl group optionally to be carried out is likewise effected in a manner known per se. For example, the carboxylic acid to be esterified is treated with excess alcohol, especially one of those specified above, in the presence of a dehydrating agent, particularly a symmetrically substituted carbodiimide, such as N,N'-dicyclohexyl carbodiimide, or in the presence of an acid catalyst, for example a strong inorganic acid; or the free acid is first converted into a reactive derivative, such as chloride or anhydride, and this is reacted with the desired alcohol. The claimed esters, especially methyl esters, may also advantageously be produced by reacting the free carboxylic acid to be esterified with the corresponding diazo-lower alkane, especially diazomethane.

Wherever mention is made in this description of acid catalysis without further specific details, it shall be understood as meaning treatment in the presence of an inorganic acid, for example sulphuric acid, perchloric acid or a hydrohalic acid, such as hydrochloric, hydrobromic or hydriodic acid, or especially of an organic acid, for example a sulphonic acid, such as, especially, p-toluenesulphonic acid, or of a relatively strong carboxylic acid, such as oxalic acid or formic acid.

The free 19-hydroxyl group of the 10β-hydroxymethyl group may also be oxidised in a manner known per se to form the 19-oxo group of the 10β-formyl group. Preferred oxidising agents for this process are compounds of hexavalent chromium, such as chromium trioxide or chromic acid and its alkali metal salts, and the reaction medium used is advantageously lower alkanecarboxylic acids, such as acetic or propionic acid, or pyridine or acetone, optionally diluted with a halogenated lower alkane, such as dichloromethane or chloroform, and the reaction temperature is preferably kept below room temperature. Both hydroxymethyl group and the formyl group can be further oxidised by the said chromium compounds to form the carboxyl radical, for which purpose it is advantageous to use extended reaction times, temperatures at, or slightly above, room temperature (not above about 50° C.), and/or aqueous sulphuric acid as solvent for the oxidising agent.

Derivatives having a protected 3- and/or 20-oxo group and corresponding to the compounds of the formula I can advantageously be obtained using known 19,21-dihydroxypregn-4-ene-3,20-dione or 19-hydroxyandrost-4-ene-3,17-dione compounds as starting material and employing the above-described known general processes, especially the conversion of the $R^3$ group with protection of the oxo groups.

The invention also relates to those embodiments of the above processes in which a compound obtained as intermediate in any stage is used as starting material and the remaining stages are carried out, or in which a starting material is formed under the reaction conditions.

The pharmaceutical preparations of the present invention containing the compounds of the formula I can be used in particular for the treatment of hyperaldosteronism of a wide variety of forms. They contain an effective amount of the active substance alone or in admixture with inorganic or organic, solid or liquid, pharmaceutically usable excipients, and, if desired, also with other pharmacologically or therapeutically valuable substances, and are suitable especially for enteral, for example oral or rectal, or for parenteral administration.

Throughout the entive remainder of the description the term "active substance⇌ shall be understood to mean a compound of the formula I as defined initially in connection with the pharmaceutical preparations according to the invention by the general and especially specified meanings.

The present invention relates in particular to pharmaceutical compositions containing as active substance at least one of the compounds of the formula I (including 1,2-dehydro derivatives and salts) according to the invention in the form of a sterile and/or isotonic aqueous solution, or in admixture with at least solid or semi-solid excipient.

The present invention also relates to medicinal preparations in the form of dosage units that contain at least one of the compounds according to the invention alone or in admixture with one or more excipients, especially medicinal preparations in solid form.

The invention relates in particular to medicinal preparations in the form of tablets (including lozenges, granules and pastilles), sugar-coated tablets, capsules, pills, ampoules, dry phials or suppositories containing at least one of the active substances of the formula I alone or in admixture with one or more excipients.

The term "medicinal preparation" is used in this description to mean individual separate portions of homogeneous composition that are suitable for medicinal administration. The expression "medicinal preparation in the form of dosage units" is used in this description to mean individual separate portions of homogeneous compositions that are suitable for medicinal administration and that each contain a specific amount of the active substance of the invention corresponding to about 0.025 to about 4, preferably about 0.1 to about 1, daily dose.

The excipients for use in the pharmaceutical compositions (for example granulates) for the production of tablets, sugar-coated tablets, capsules and pills are, for example, as follows:

(a) diluents, for example starch, sugars, such as lactose, glucose and saccharose, mannitol, sorbitol and silica;

(b) binders, for example carboxymethylcellulose and other cellulose derivatives, alginic acid and its salts, such as sodium alginate, gelatin, and polyvinylpyrrolidone;

(c) moisture regulators, for example glycerin;

(d) disintegrators, for example agar-agar, calcium carbonate and sodium bicarbonate;

(e) retardants for slowing down the absorption of the active substance, for example paraffin;

(f) accelerators for the resorption, for example quaternary ammonium compounds;

(g) surfactants, for example cetyl alcohol and glycerin monostearate;

(h) adsorbents, for example kaolin and bentonite;

(i) glidants and lubricants, for example talcum, calcium stearate, magnesium stearate and solid polyethylene glycols.

These and similar excipients can also be used for several of the above-mentioned purposes.

The tablets, sugar-coated tablets, capsules and pills containing the above-mentioned pharmaceutical compositions according to the invention can be provided with the customary coatings and coating materials with which, if desired, dyes or pigments, for example for identification or characterisation purposes, are admixed. These coatings can also be of a composition that makes possible a retarted release of the active substance; waxes and cellulose preparations, such as acetylcellulose phthalate or hydroxypropylmethylcellulose phthalate, for example, are suitable for this purpose.

These compositions can also be processed to microcapsules.

Medicinal preparations for parenteral administration are preferably ampoules containing a single dose of the active substance of the invention, especially a water-soluble, physiologically tolerable salt, in the form of an aqueous solution that is preferably sterilised, and they optionally contain the usual buffers and/or neutral inorganic salts such as sodium chloride, as adjwants for adjusting the isotonicity with blood. An aqueous solution of this type is also particularly suitable for the production of injectable solid forms of medicinal preparation, such as dry phials into which the quantity of solution corresponding to the single dose is evaporated in the usual manner, for example by lyophilisation, and the solid residue is brought into the injection solution, with sterile water, only immediately before use.

Suitable excipient for pharmaceutical compositions to be processed into suppositories are the customary suppository base materials, for example natural or synthetic triglycerides, such as cocoa butter, paraffin hydrocarbons, polyethylene glycols and higher alkanols. Gelatin rectal capsules contain as base material, for example, liquid triglycerides, polyethylene glycols or paraffin hydrocarbons.

The pharmaceutical compositions of the invention preferably contain from about 0.1 to about 99.5%, especially from about 1 to about 90%, by weight of the active substance.

The recommended daily dosage for a warm-blooded animal weighing 75 kg is approximately 5–500 mg, preferably approximately 20–300 mg, but it can vary within wide limits depending on species, age and the individual response.

The production of the above-mentioned pharmaceutical compositions, preparations, medicinal preparations and medicinal preparations in the form of dosage units according to the invention is carried out by means of conventional manufacturing processes in the pharmaceutical industry that are known per se, for example by means of customary mixing, granulating, tabletting, sugar-coating and dissolving and lyophilising processes, which are carried out, if desired, under sterile conditions or an intermediate or an end product is sterilised.

The present invention also relates to the use of compounds of the formula I for alleviating a wide variety of forms of hyperaldosteronism in man and other warm-blooded animals, and to a corresponding therapeutic method that is characterised by administering an effective dosage of at least one of the active substances according to the invention alone or together with one or more pharmaceutical excipients or in the form of a medicinal preparation. The active substances according to the invention are administered enterally, for example rectally or especially orally, or parenterally, such as intraperitoneally or intravenously.

In the following Examples, which illustrate the invention further without limiting it, the temperatures are in degrees Centigrade.

EXAMPLE 1

A solution of 1.70 g of 19,21-dihydroxypregn-4-ene-3,20dione 19,21-diacetate [Chem. Pharm. Bull. (Tokyo) 6, 325 (1958)] and 2.5 g of chloranil in 50 ml of methanol is heated under reflux for 4 hours, concentrated in vacuo to approximately a third and diluted with approximately 400 ml of ethyl acetate. The solution is freed of solid impurities by filtration, washed with a saturated solution of sodium dithionite in N sodium hydroxide solution and subsequently with a saturated aqueous sodium chloride solution, dried with sodium sulphate and concentrated in vacuo. The residue is chromatographed over silica gel; elution with a mixture of hexane and ethyl acetate (3:1) yields purified 19,21-dihydroxypregna-4,6-diene-3,30-dione diacetate which is suitable for further processing (cf. Example 2). Melting point: 152°–154° (from methylene chloride/ether).

In an analogous manner, starting with a corresponding 4,5-unsaturated 3-oxo compound, the following compounds can be obtained:

19,21-dihydroxypregna-4,6-diene-3,20-dione; melting point: 161°–164°;

19,21-dihydroxypregna-4,6-diene-3,20-dione 21-acetate;

19,21-dihydroxypregna-4,6-diene-3,20-dione 19-acetate 21-benzoate;

19,21-dihydroxypregna-4,6-diene-3,20-dione 19,21-dibutyrate, amorphous;

19,21-dihydroxypregna-4,6-diene-3,20-dione 19-formate 21-benzoate;

21-hydroxy-19-methoxypregna-4,6-diene-3,20-dione 21-acetate, melting point: 159°–161°;

$[\alpha]_D = +176°$ (c=0.5, chloroform);

21-hydroxy-3,20-dioxopregna-4,6-diene-19-oic acid and its acetate, butyrate and benzoate;

methyl 21-hydroxy-3,20-dioxopregna-4,6-diene-19-oate and its acetate and propionate.

EXAMPLE 2

A solution of 1.4 g of the 19,21-dihydroxypregna-4,6-diene-3,20-dione diacetate obtained according to Example 1 in 80 ml of methanol is mixed with a solution of 1.0 g of sodium bicarbonate in 20 ml of water, the mixture is stirred for 4 hours at room temperature under an argon atmosphere, and subsequently concentrated in vacuo. The residue is distributed between methylene chloride and water and the organic phase is washed with a sodium chloride solution, dried with sodium sulphate and concentrated by evaporation.

Chromatography over silica gel and elution with a mixture of hexane and ethyl acetate (1:1) yields 19,21-dihydroxypregna-4,6-diene-3,20-dione 19-acetate, which after dissolving and allowing to crystallise from methylene chloride/isopropyl ether has a melting point of 100°–130°.

EXAMPLE 3

A solution of 211 mg of sodium bicarbonate in 2.6 ml of water is added to a solution of 100 mg of 19,21-dihydroxypregna-4,6-diene-3,20-dione diacetate in 6.5 ml of methanol and the mixture is heated under reflux for 3 hours and concentrated in vacuo. A solution of the residue in methylene chloride is washed with a 15% aqueous sodium chloride solution, dried with sodium sulphate and concentrated in vacuo. The residue is taken up in a mixture of hexane and ethyl acetate (1:1) and chromatographed over silica gel. After evaporating off the solvent, the product is dissolved and allowed to crystallise from methylene chloride/diethyl ether/diisopropyl ether, yielding 19,21-dihydroxypregna-4,6-diene-3,20-dione, melting point: 161°–164°.

EXAMPLE 4

A solution of 500 mg of 19,21-dihydroxypregna-4,6-diene-3,20-dione 19-acetate in 14 ml of methanol and 0.8 ml of thioacetic acid is refluxed for one hour, cooled to room temperature, and water is added until the solution becomes turbid. The reaction mixture is evaporated to dryness in vacuo at a maximum temperature of 45°, and the residue is chromatographed over silica gel. Elution with a mixture of hexane and acetone (4:1) yields the chromatographically uniform 7α-acetylthio-19,21-dihydroxypregn-4-ene-3,20-dione 19-acetate, which is obtained in amorphous form by lyophilisation from aqueous methanol. IR spectrum (in methylene chloride): 3460, 2950, 1740, 1690, 1670, 1625, 1385, 1365, 1355, 1335, 1230, 1120, 1080, 1040, 955, 910 cm$^{-1}$.

In an analogous manner, 21-hydroxy-19-methoxypregna-4,6-diene-3,20-dione 21-acetate yields 7α-acetylthio-21-hydroxy-19-methoxypregn-4-ene-3,20-dione 21-acetate in amorphous form (precipitated from aqueous methanol); $[\alpha]_D = +78°$ (c=0.5, chloroform) IR spectrum (in methylene chloride): 2950, 1745, 1720, 1690, 1670, 1620, 1375, 1360, 1235, 1120, 1085, 965 cm$^{-1}$.

EXAMPLE 5

A solution of 2.6 g of 6β,19-epoxy-21-hydroxypregn-4-ene-3,20-dione 21-acetate and 1.3 g of p-toluenesulphonic acid in 26 ml of methylene chloride and 5.2 ml of acetic anhydride is stirred for 16 hours at 45° and subsequently poured onto an ice-cold solution of 13.5 g of sodium acetate in 130 ml of water while stirring. The aqueous layer, after separation of the organic layer, is extracted with ethyl acetate, the combined organic extracts are washed with water, aqueous sodium bicarbonate solution and water in succession, dried and concentrated by evaporation. Crystallisation from methylene chloride/ether of the crude product obtained yields 19,21-dihydroxypregna-4,6-diene-3,20-dione 19,21-diacetate having a melting point of 152°–154°.

In an analogous manner, but using an equivalent amount of butyric acid anhydride, 19,21-dihydroxypregna-4,6-diene-3,20-dione 19-butyrate 21-acetate is obtained.

EXAMPLE 6

(a) A solution of potassium tert.-butoxide is prepared from 34 g of potassium and 980 ml of tert.-butanol under an argon atmosphere; to this solution a solution of 45 g of 3,3-ethylenedithio-19-hydroxyandrosta-4,6-dien-17-one in 1000 ml of 1,2-dimethoxyethane is quickly added dropwise at room temperature under an argon atmosphere while stirring. After stirring for 15 minutes, a solution of 35.5 g of tosylmethyl isocyanide in 1000 ml of 1,2-dimethoxyethane is added to the reaction mixture over a period of 90 minutes at 25° and the mixture is stirred for a further hour and poured onto ice water. The organic layer is separated, the aqueous layer is extracted with methylene chloride and the combined organic extracts are washed with water, dried over sodium sulphate and concentrated in a water-jet vacuum. The residue is chromatographed over a silica gel column; elution with a mixture of hexane and ethyl acetate (4:1) yields 24 g of 3,3-ethylenedithio-17β-cyanoandrosta-4,6-dien-19-ol; melting point: 180°–181° after crystallisation once from methylene chloride/diisopropyl ether; $[\alpha]_D = 162°$ (c=0.14, chloroform). Further elution with the same solvent mixture yields 12 g of 3,3-ethylenedithio-17α-cyanoandrosta-4,6-dien-19-ol; melting point: 211°–213° (from methylene chloride/ethyl acetate); $[\alpha]_D = 61°$ (c=0.48, chloroform).

(b) 400 ml of a 20% solution of diisobutyl aluminum hydride in toluene is added dropwise at −20° over a period of 15 minutes, while stirring, to a solution of 24 g of 3,3-ethylene-dithio-17β-cyanoandrosta-4,6-dien19-ol in 450 ml of 1,2-dimethoxyethane, the mixture is allowed to warm to 25° and is stirred for a further hour at this temperature. The reaction mixture is poured onto ice water, acidified with hydrochloric acid and stirred for one hour. The product is taken up in methylene chloride, the organic phase is washed in succession with water, aqueous sodium bicarbonate solution and water, dried over sodium sulphate and concentrated in a waterjet vacuum. The residue is chromatographed over a silica gel column; elution with a mixture or toluene and ethyl acetate (95:5) yields 3,3-ethylenedithio-19-hydroxyandrosta-4,6-diene-17β-carboxaldehyde; melting point: 165°–166° (from methylene chloride/diisopropyl ether), $[\alpha]_D = +198°$ (c=0.474, chloroform).

(c) 13.5 ml of a 1.6 molar solution of butyl lithium in hexane is added dropwise to a solution of 6.7 ml of formaldehyde dimethylthioacetal S-oxide (methylthiomethyl methyl sulphoxide) in 80 ml of tetrahydrofuran at −20° under an argon atmosphere, so that the temperature does not exceed −17°. Subsequently a solution of 13 g of 3,3-ethylenedithio-19-hydroxyandrosta-4,6-diene-17β-carboxaldehyde in 100 ml of tetrahydrofuran is added dropwise to the reaction mixture over a period of 30 minutes and the mixture is stirred for a further 30 minutes. The reaction mixture is poured onto ice water and the product is taken up on ethyl acetate. The combined organic extracts are washed with water and a saturated aqueous sodium chloride solution in succession, dried over sodium sulphate, concentrated in a water-jet vacuum and the residue is applied to a column of silica gel. The unreacted starting material is recovered by eluting with a mixture of hexane and ethyl acetate (1:1); using a mixture of ethyl acetate/acetone (2:1) fractions are eluted that after evaporation yield a crystalline mixture of isomeric 3,3-ethylenedithio-21ξ-methylsulphinyl-21ξ-methylthiopregna4,6-diene-19,20-ξ-diols, which is processed further without separation.

(c) 42 ml of water, 12 g of mercury(II) chloride and 12 g of cadmium carbonate are added to a solution of 15.9 g of the mixture of isomers obtainable according to (c) in 960 ml of acetone, and the mixture is stirred at room temperature for 5 hours and filtered through a layer of kieselguhr. The filter cake is extracted with methylene chloride, the extract is combined with the original filtrate and concentrated by evaporation. The resulting crude mixture of isomeric 19,20ξ-dihydroxy-21ξ-methylsulphinyl-21ξ-methylthiopregna-4,6-dien-3-ones is used directly in the next stage.

(c) 50 ml of 5 N hydrochloric acid is added to the isomeric mixture of stage (d) dissolved in 300 ml of tetrahydrofuran, and the mixture is stirred for 13 hours at room temperature. The reaction mixture is poured onto 2 liters of ice-water and the product is taken up in methylene chloride. The combined extracts are washed with a dilute sodium carbonate solution, water and a saturated sodium chloride solution in succession, dried over sodium sulphate and concentrated in a water-jet vacuum. The residue is chromatographed over a silica gel column; elution with a mixture of hexane and acetone (2:1) yields 19,21-dihydroxypregna-4,6-diene-3,20-dione, which after crystallisation from acetone/hexane melts at 163°–165° and is identical with the product in Examples 1 and 3.

EXAMPLE 7

1.6 ml of benzoyl chloride is added to a solution and 384 mg of 19,21-dihydroxypregna-4,6-diene-3,20-dione 19-acetate in 3 ml of pyridine, the mixture is allowed to stand at room temperature for 30 minutes and poured onto ice water. After stirring for 15 minutes the reaction mixture is extracted with ethyl acetate, the organic phase is washed in succession with a dilute sodium carbonate solution, 1 N-hydrochloric acid and with water, dried over sodium sulphate and concentrated in a waterjet vacuum. The resulting 19,21-dihydroxypregna-4,6-diene-3,20-dione 19-acetate 21-benzoate has a melting point of 120°–121° after dissolving and allowing to crystallise from methylene chloride/diisopropyl ether.

In the same manner using the same quantities by weight of the starting material and reagents, the following esters of 19,21-dihydroxypregna-4,6-diene-3,20-dione are obtained: with propionic anhydride, the oily 19-acetate 21-propionate; IR spectrum (in methylene chloride): 2950, 1740, 1725, 1615, 1365, 1225, 1180, 1080, 1035, 880 cm$^{-1}$; with valeric anhydride, the oily 19-acetate 21-valerate; IR spectrum (in methylene chloride): 2950, 1740, 1725, 1660, 1620, 1585, 1370, 1225, 1170, 1100, 1035, 880 cm$^{-1}$; and with pivaloyl chloride, the oily 19-acetate 21-pivalate; IR spectrum (in methylene chloride): 2950, 1735, 1720, 1655, 1615, 1585, 1365, 1225, 1160, 1100, 1035, 890 cm$^{-1}$.

EXAMPLE 8

A solution of 180 mg of sodium bicarbonate in 3.6 ml of water is added to a solution of 300 mg of the 19,21-dihydroxypregna-4,6-diene-3,20-dione 19-acetate 21-pivalate (obtainable according to Example 7) in 18 ml of methanol, the mixture is stirred for 4 hours at 45° and evaporated to dryness in a water-jet vacuum. The residue is taken up in ethyl acetate, washed with water, dried over sodium sulphate and concentrated by evaporation. Crystallisation from methylene chloride/diisopropyl ether yields 19,21-dihydroxypregna-4,6-diene-3,20-dione 21-pivalate having a melting point of 173°–174°.

EXAMPLE 9

0.25 ml of concentrated hydrochloric acid is added to a solution of 100 mg of 19,21-dihydroxy-17α-pregna-4,6-diene-3,20-dione 19,21-diacetate (obtainable by processing the 3,3-ethylenedithio-17α-cyanoandrosta-4,6-dien-19-ol described in Example 6a in accordance with the process steps b-e in Example 6) in 2.5 ml of ethanol and the mixture is refluxed for 30 minutes. The volatile constituents of the reaction mixture are removed by evaporating in a water-jet vacuum, the residue is dissolved in 1 ml of pyridine and treated with 0.5 ml of acetic anhydride. After standing at room temperature for 17 hours, the mixture is concentrated in vacuo, the residue is dissolved in ethyl acetate, washed in succession with 1 N hydrochloric acid, a dilute sodium bicarbonate solution and water, dried over sodium sulphate and concentrated by evaporation. The residue is chromatographed over a column of silica gel: elution with a mixture of hexane, ethyl acetate and acetone (12:2:1) yields initially a small fore-run of the recovered starting material, which is followed by the main fraction of the desired 19,21-dihydroxy-pregna-4,6-diene-3,20-dione 19,21-diacetate. The product is identical with that of Example 5; melting point: 152°–154° (from methylene chloride/ether).

EXAMPLE 10

Tablets containing approximately 50 mg of active substance, for example 19,21-dihydroxypregna-4,6-diene-3,20-dione or the 19,21-diacetate thereof, are produced as follows:

| Composition for 1000 tablets | |
| --- | --- |
| active substance, very finely ground | 50.0 g |
| powdered sugar (saccharose) | 79.0 g |
| gum arabic | 4.75 g |
| sorbitol | 3.75 g |
| talc | 2.5 g |
| magnesium stearate | 4.9 g |
| mineral oil | 0.1 g |
| carboxymethylcellulose (Na salt) | 5.0 g |

Production

The active substance is mixed with the powdered sugar and the gum arabic, sieved and granulated by means of an approximately 35% aqueous sorbitol solution. The granulate is forced through a sieve, dried, sieved again, and thoroughly mixed with the remaining auxiliaries (talc, magnesium stearate, mineral oil and carboxymethylcellulose sodium salt). The mixture is compressed in the usual manner to form 150 mg tablets.

EXAMPLE 11

Gelatin capsules containing approximately 25 mg of active substance, for example 19,21-dihydroxypregna-4,6-diene-3,20-dione or the 19,21-diacetate thereof, are produced as follows:

| Composition for 1000 capsules | |
| --- | --- |
| active substance, very finely ground | 25 g |
| lactose, very finely ground | 25 g |

The active substance and the lactose are thoroughly mixed, triturated and sieved, and the powder obtained is introduced in portions of 50 mg each into gelatin capsules.

EXAMPLE 12

Tablets containing approximately 100 mg of active substance, for example 19,21-dihydroxypregna-4,6-diene-3,20-dione or its 19-acetate or 19,21-diacetate, are produced in the following manner:

| Composition of one tablet: | |
| --- | --- |
| active substance, micronised | 100.0 mg |
| corn starch | 50.0 mg |
| silica, colloidal | 5.0 mg |
| gelatin | 5.0 mg |
| microcrystalline cellulose | 80.0 mg |
| sodium carboxymethylstarch | 20.0 mg |
| magnesium stearate | 1.5 mg |
| | 361.5 mg. |

Production of 10000 tablets 1 kg of micronised active substance and 0.5 kg of corn starch are mixed with 0.05 kg of colloidal silica and worked into a moist composition with a solution of 0.05 kg of gelatin in 0.5 kg of distilled water (30° C.). This mixture is forced through a sieve having a mesh width of 3 mm and dried for 30 minutes at 45° C. (fluidised bed drier). The dry granulate is pressed through a sieve having a mesh width of 0.8 mm, mixed with a previously sieved mixture of 0.8 kg of microcrystalline cellulose and 0.2 kg of sodium carboxymethyl-starch and with 0.015 kg of magnesium stearate and compressed to tablets weighing 361.5 mg.

EXAMPLE 13

Sugar-coated tablets containing about 100 mg of active substance, for example, 19,21-dihydroxypregna-4,6-diene-3,20-dione or its 19-acetate or 19,21-diacetate, are produced as follows:

| Composition of a sugar-coated tablet core: | |
| --- | --- |
| active substance, micronised | 100.0 mg |
| corn starch | 90.0 mg |
| tricalcium phosphate | 100.0 mg |
| polyvinylpyrrolidone K 25 | 15.0 mg |
| magnesium stearate | 2.0 mg |
| sodium carboxymethycellulose | 33.0 mg |

| Composition of a sugar-coated tablet core: |
| --- |
| 340.0 mg |

Production of 50.000 sugar-coated tablet cores

The mixture of 5 kg of micronised active substance, 4.5 kg of corn starch and 5 kg of tricalcium phosphate is granulated with a solution of 0.75 kg of polyvinylpyrrolidone K 25 in 5 kg of distilled water in a fluidised bed process. The granulate, which is dried at 45° and pressed through a sieve having a mesh width of 1 mm, is mixed with 0.1 kg of magnesium stearate and 1.65 kg of sodium carboxymethylstarch, and the mixture is compressed to 340 mg domes tablets.

Production of 6,6 kg sugar-coated tablets 6 kg of the sugar-coated tablet cores are coated in portions in a coating pan of 45 cm diameter with a sugar syrup (2 parts sugar and 1 part by weight of distilled water), in which 1.5% polyvinylpyrrolidone K 25 and 1% polyethylene glycol 6000 are dissolved and 20% of talc is suspended, until a weight of 410 mg is reached, drying being carried out inbetween with warm air of approximately 60°. Subsequently sugar syrup (2 parts of sugar and 1 part of water) is applied in portions until a final weight of 450 mg is achieved. The sugar-coated tablets are finally glazed with a solution of 2% carnauba wax in trichloroethylene.

EXAMPLE 14

Soft gelatin capsules containing 50 mg of active substance, for eample 19,21-dihydroxypregna-4,6-diene-3,20-dione or its 19-acetate or 19,21-diacetate, are obtained as follows:

| Composition of a soft gelatin capsule: | |
| --- | --- |
| active substance, micronised | 50.0 mg |
| soya lecithin | 1.5 mg |
| beeswax | 2.5 mg |
| vegetable oil | 110.0 mg |
| vegetable oil, partially hydrogenated | 54.0 mg |
| | 218.0 mg |

Production of 100,000 soft gelatin capsules 5.0 kg of micronised active substance are suspended in a mixture, produced by melting, of 0.15 kg of soya lecithin, 0.25 kg of beeswax, 5.4 kg of partially hydrogenated vegetable oil and 11 kg of vegetable oil and made into gelatin capsules by a stamping process. The gelatin casing consists of approximately 71% gelatin, approximately 28% glycerin (85%) and approximately 1% titanium dioxide as well as 0.3% of p-hydroxybenzoic acid propyl ester. The size of the capsule is 4 minims (oblong shape).

EXAMPLE 15

Film-coated tablets, containing 100 mg of active subtance, for example 19,21-dihydroxypregna-4,6-diene-3,20-dione or its 19-acetate or 19,21-diacetate, are produced as follows:

| Composition of a film-coated tablet core: | |
| --- | --- |
| active substance, micronised | 100.0 mg |
| polyethylene glycol 6000 | 52.0 mg |
| colloidal silica | 5.0 mg |
| stearic acid | 3.0 mg |
| | 160.0 mg |

Production of 10,000 cores 1.0 kg of micronised active substance is mixed with a melt of 0.52 kg of polyethylene glycol [prepared with the addition of 0.05 kg of colloidal silica (specific surface area of 200 m$^2$/g)] and after cooling is pressed through a sieve having a mesh width of 1 mm. 0.03 kg of pulverulent, previously sieved stearic acid is admixed with the granulate and the mixture is compressed to 160 mg slightly domed tablets.

Production of 30,000 film-coated tablets 4.8 kg of cores are sprayed in a dragee-coating vessel of 45 cm diameter, with a continuous supply of air of 35°, with a solution of hydroxypropylmethylcellulose (viscosity 6 cP, 2% solution in water) in distilled water, in which 2% talc is suspended, until there is 5 mg of coating on each core.

I claim:

1. A 19-oxygenated steroid of the pregnane series having the formula I

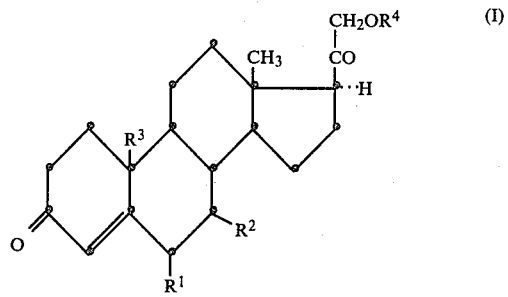

in which

R$^1$ represents a hydrogen atom;

R$^2$ represents an α-oriented lower alkanoylthio group;

R$^3$ represents hydroxymethyl, hydroxymethyl etherified by lower alkyl or hydroxymethyl esterified by lower alkanoyl; and R$^4$ represents a hydrogen atom or the acyl radical of benzoic acid or an aliphatic monocarboxylic acid having 1–8 carbon atoms.

2. A compound as claimed in claim 1, in which formula

R$^1$ represents a hydrogen atom;

R$^2$ represents α-oriented acetylthio;

R$^3$ represents hydroxymethyl, or hydroxymethyl esterified by lower alkanoyl; and R$^4$ represents a hydrogen atom or lower alkanoyl.

3. 7α-Acetylthio-19,21-dihydroxypregn-4-ene-3,20-dione 19-acetate.

4. 7α-Acetylthio-21-hydroxy-19-methoxypregn-4-ene-3,20-dione 21-acetate.

5. An aldosterone-antagonizing pharmaceutical composition comprising a correspondingly effective amount of a compound of formula I

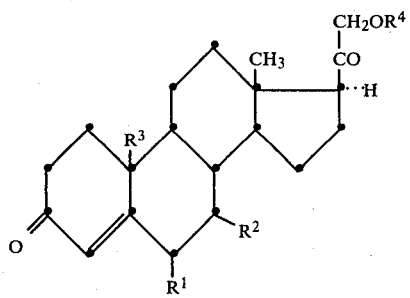

(I)

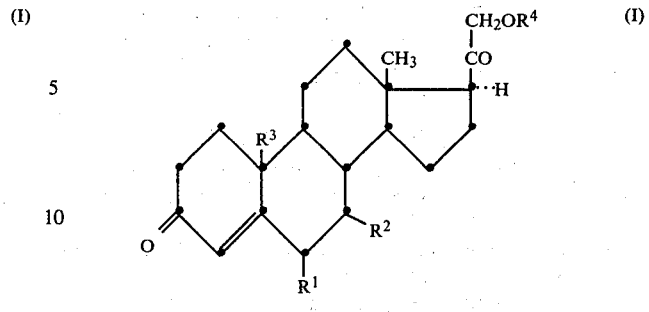

(I)

in which
- $R^1$ represents a hydrogen atom;
- $R^2$ represents an α-oriented lower alkanoylthio group, or
- $R^3$ represents hydroxymethyl, hydroxymethyl etherified by lower alkyl or hydroxymethyl esterified by lower alkanoyl; and
- $R^4$ represents a hydrogen atom or the acyl radical of benzoic acid or an aliphatic monocarboxylic acid having 1–8 carbon atoms; together with a pharmaceutical excipient.

6. A composition according to claim 5, in which effective compound $R^1$ represents hydrogen, $R^2$ represents α-acetylthio, $R^3$ represents hydroxymethyl or lower alkanoyloxymethyl; and $R^4$ represents hydrogen or lower alkanoyl.

7. A composition according to claim 5, comprising the 7α-acetylthio-19,21-dihydroxypregn-4-ene-3,20-dione, or the 19-acetate, 21-acetate or 19,21-diacetate thereof.

8. A composition according to claim 5, comprising 7α-acetylthio-21-hydroxy-19-methoxypregn-4-ene-3,20-dione 21-acetate.

9. A composition according to claim 5, in the form of dosage units.

10. A composition according to claim 9, in solid or semi-solid dosage units for oral administration.

11. A composition according to claim 9, containing 10–100 mg of active ingredient per dosage unit.

12. A therapeutic method for alleviating pathological conditions which are consequent to hyperaldosteronism in a warm-blooded animal which consists in the administration to said animal in need thereof of an effective amount of an aldosterone-antagonizing pharmaceutical composition comprising a correspondingly effective amount of a compound of formula I in which
- $R^1$ represents a hydrogen atom;
- $R^2$ represents an α-oriented lower alkanoylthio group, or
- $R^1$ and $R^2$ together represent a carbon-carbon bond;
- $R^3$ represents hydroxymethyl, hydroxymethyl etherified by lower alkyl or hydroxymethyl esterified by lower alkanoyl; and
- $R^4$ represents a hydrogen atom or the acyl radical of benzoic acid or an aliphatic monocarboxylic acid having 1–8 carbon atoms; or the corresponding 1,2-dehydro-derivative of said compound wherein $R^1$ and $R^2$ is a carbon-carbon bond; together with a pharmaceutical excipient.

13. A method according to claim 12, wherein the warm blooded animal is man.

14. A therapeutic method according to claim 12 in which $R^1$ and $R^2$ together represent a carbon-carbon bond; $R^3$ is hydroxymethyl or lower alkanoyloxymethyl; and $R^4$ is hydrogen or lower alkanoyl.

15. A therapeutic method according to claim 12 in which $R^1$ and $R^2$ together represent a carbon-carbon bond; $R^3$ is lower alkanoyloxymethyl and $R^4$ is lower alkanoyl.

16. A therapeutic method according to claim 12 wherein the compound of formula I is 19,21-dihydroxypregna-4,6-diene-3,20-dione.

17. A therapeutic method according to claim 12 wherein the compound of formula I is 19,21-dihydroxypregna-4,6-diene-3,20-dione 19-acetate.

18. A therapeutic method according to claim 12 wherein the compound of formula I is 19,21-dihydroxypregna-4,6-diene-3,20-dione 21-acetate.

19. A therapeutic method according to claim 12 wherein the compound of formula I is 19,21-dihydroxypregna-4,6-diene-3,20-dione 19,21-diacetate.

* * * * *